(12) United States Patent
Siegel et al.

(10) Patent No.: US 7,315,678 B2
(45) Date of Patent: Jan. 1, 2008

(54) METHOD AND APPARATUS FOR LOW-LOSS SIGNAL TRANSMISSION

(75) Inventors: Peter Siegel, La Canada, CA (US); Cavour Yeh, Los Angeles, CA (US); Fred Shimabukuro, Rancho Palos Verde, CA (US); Scott Fraser, La Canada-Flintridge, CA (US)

(73) Assignee: California Institute Of Technology, Pasadena, CA (US)

( * ) Notice: Subject to any disclaimer, the term of this patent is extended or adjusted under 35 U.S.C. 154(b) by 0 days.

(21) Appl. No.: 11/300,639

(22) Filed: Dec. 13, 2005

(65) Prior Publication Data

US 2006/0165360 A1     Jul. 27, 2006

Related U.S. Application Data

(60) Provisional application No. 60/635,846, filed on Dec. 13, 2004.

(51) Int. Cl.
G02B 6/02      (2006.01)

(52) U.S. Cl. .................. 385/125; 385/117; 385/123

(58) Field of Classification Search ............... 385/117, 385/123, 125; 333/239, 242, 248
See application file for complete search history.

(56) References Cited

U.S. PATENT DOCUMENTS

| | | | | |
|---|---|---|---|---|
| 4,458,229 A | * | 7/1984 | Landry et al. | 333/248 |
| 5,638,478 A | * | 6/1997 | Iwakura et al. | 385/111 |
| 6,975,898 B2 | * | 12/2005 | Seibel | 600/473 |
| 2004/0175082 A1 | * | 9/2004 | Birks et al. | 385/123 |

FOREIGN PATENT DOCUMENTS

| | | | |
|---|---|---|---|
| EP | 1541090 A1 | * | 6/2005 |
| WO | WO 2002/101430 A1 | * | 12/2002 |
| WO | WO 2002101430 A1 | * | 12/2002 |

OTHER PUBLICATIONS

B.J. Mangan, L. Farr, A. Langford, P.J. Roberts, D.P. Williams, F. Couny, M. Lawman, M. Mason, S. Coupland, R. Flea, H. Sabert, T.A. Birks, J.C. Knight and P. J. Russell, "Low loss (1.7dB/km) hollow core photonic bandgap fiber," Optical and Fiber Comm. Conf (OFC-2004) post deadline paper PDP24, Los Angeles, CA, Feb. 22-27, 2004.

(Continued)

*Primary Examiner*—Frank G. Font
*Assistant Examiner*—Hung Lam
(74) *Attorney, Agent, or Firm*—Tope-McKay & Associates

(57) ABSTRACT

The present invention relates to the field of radio-frequency (RF) waveguides. More specifically, the present invention pertains to a method and apparatus that provides ultra-low-loss RF waveguide structures targeted between approximately 300 GHz and approximately 30 THz. The RF waveguide includes a hollow core and a flexible honeycomb, periodic-bandgap structure surrounding the hollow core. The flexible honeycomb, periodic-bandgap structure is formed of a plurality of tubes formed of a dielectric material such as of low-loss quartz, polyethylene, or high-resistivity silicon. Using the RF waveguide, a user may attach a terahertz signal source to the waveguide and pass signals through the waveguide, while a terahertz signal receiver receives the signals.

21 Claims, 6 Drawing Sheets

OTHER PUBLICATIONS

T.A. Birks, D. Mogilevtsev, J.C. Knight and P.J. Russell, "Dispersion compensation using single-material fibers," IEEE Photonics Technology Letters, vol. 11, No. 6, pp. 674-676, Jun. 1999.

Philip Russell, "Photonic Crystal Fibers," Science, v.299, pp. 358-362, Jan. 17, 2003.

G. Humbert, J.C. Knight, G. Bouwmans, P. J. Russell, D.P. Williams, P.J. Roberts and B.J. Mangan, "Hollow core photonic crystal fibers for beam delivery," Optics Express, vol. 12, No. 8, pp. 1477-1484, Apr. 19, 2004.

J.C. Knight, T.A. Birks, P.J. Russell and D.M. Atkin, "All-silica single-mode optical fiber with photonic crystal cladding," Optics Letters, vol. 21, No. 19, pp. 1547-1549, Oct. 1, 1996.

G. Humbert, J.C. Knight, G. Bouwmans, P. J. Russell, D.P. Williams, P.J. Roberts and B.J. Mangan, "Hollow core photonic crystal fibers for beam delivery," Optics Express, vol. 12, No. 8, pp. 1477-1484, A9 Apr. 2004.

H. Han, H. Park, M. Cho, J. Kim, I. Park and H. Lim, "Terahertz pulse propagation in plastic photonic crystal fibers," 2002 IEEE MTT-S Int. Mic. Sym. Digest, vol. 2, pp. 1075-1078, Jun. 7, 2002.

* cited by examiner

METHOD AND APPARATUS FOR LOW-LOSS SIGNAL TRANSMISSION

PRIORITY CLAIM

The present application claims the benefit of priority of U.S. Provisional Patent Application No. 60/635,846, filed Dec. 13, 2004, and entitled "Hollow-core periodic bandgap flexible dielectric waveguide for low-loss THz signal transmission."

STATEMENT OF GOVERNMENT INTEREST

The invention described herein was made in the performance of work under a NASA contract, and is subject to the provisions of Public Law 96-517 (35 USC 202) in which the Contractor has elected to retain title.

BACKGROUND OF THE INVENTION (1) Technical Field

The present invention relates to the field of radio-frequency (RF) waveguides. More specifically, the present invention pertains to a method and apparatus that provides ultra-low-loss (less than 1 dB per meter) RF waveguide structures targeted between 300 GHz and 30 THz.

(2) Background

RF waveguides are based on the theory of wave propagation. The theory of wave propagation in periodic structures was developed several years ago. That theory provided fundamental understanding in solid-state physics and x-ray diffraction. Since then, the theory has been expanded for many other applications, such as traveling wave tubes, bandpass filters, distributed feedback lasers, integrated optics structures, dichroic plates, artificial dielectrics, etc. Most recently, photonic periodic structures (or photonic crystals) using the same basic theory have been developed for a wide range of traveling wave applications in both the microwave and optical regions of the electromagnetic spectrum. The periodic nature of the photonic crystal elements allows propagation over a restricted band of wavelengths, thus allowing filters, couplers, power splitters, waveguides and many other components, to be realized. The constructions that give rise to this frequency-dependent behavior are commonly termed "photonic bandgap structures" (PBG structures).

Hollow core photonic bandgap fiber has been developed in large part by P. J. Russell, J. C. Knight and colleagues at the University of Bath (located at BA2 7AY, United Kingdom) over the past 10 years, as disclosed in the following papers:

(1) Philip Russell, "Photonic Crystal Fibers," Science, v.299, pp. 358-362, Jan. 17, 2003.

(2) G. Humbert, J. C. Knight, G. Bouwmans, P. J. Russell, D. P. Williams, P. J. Roberts and B. J. Mangan, "Hollow core photonic crystal fibers for beam delivery," Optics Express, Vol. 12, no. 8, pp. 1477-1484, 19 Apr., 2004.

(3) B. J. Mangan, L. Farr, A. Langford, P. J. Roberts, D. P. Williams, F. Couny, M. Lawman, M. Mason, S. Coupland, R. Flea, H. Sabert, T. A. Birks, J. C. Knight and P. J. Russell, "Low loss (1.7 dB/km) hollow core photonic bandgap fiber," Optical and Fiber Comm. Conf (OFC-2004) post deadline paper PDP24, Los Angeles, Calif., Feb. 22-27, 2004.

(4) T. A. Birks, D. Mogilevtsev, J. C. Knight and P. J. Russell, "Dispersion compensation using single-material fibers," IEEE Photonics Technology Letters, vol. 11, no. 6, pp. 674-676, June 1999.

(5) J. C. Knight, T. A. Birks, P. J. Russell and D. M. Atkin, "All-silica single-mode optical fiber with photonic crystal cladding," Optics Letters, vol. 21, no. 19, pp. 1547-1549, Oct. 1, 1996.

These investigators have targeted the optical fiber community, especially the near infrared, and optimized hollow core (HC)-PBG structures for both low-loss and high power continuous wave (CW) and pulsed propagation between 1 and 2 microns, with potential extension to 10 microns wavelength.

The article by Knight and Russell et al. discloses a hollow core photonic bandgap fiber developed for 1.5 micron propagation. The core is 20 microns in diameter and the honeycomb is approximately 4 microns. The material employed is silica and the structures are extruded through a mandrel in a hot-melt process, allowing for the fabrication of many geometries.

Knight and Russell et al. developed another optical HC-PBG design, which is disclosed in G. Humbert, J. C. Knight, G. Bouwmans, P. J. Russell, D. P. Williams, P. J. Roberts and B. J. Mangan, "Hollow core photonic crystal fibers for beam delivery," Optics Express, Vol. 12, no. 8, pp. 1477-1484, A9 April, 2004. This second design disclosed a reduced diameter core and substantially higher propagation loss. Knight and Russell et al. focused on 7-cell and 19-cell core designs.

The idea of using photonic bandgap structures for terahertz waveguide propagation was published by H. Han, H. Park, M. Cho and J. Kim, in "Terahertz pulse propagation in plastic photonic crystal fibers," Lasers and Electro-Optics, 2001 and CLEO/Pacific Rim 2001, Volume: Supplement, paper WIPD1-10, pp. 22-23, 19 Jul. 2001, and later embellished in H. Han, H. Park, M. Cho, J. Kim, I. Park and H. Lim, "Terahertz pulse propagation in plastic photonic crystal fibers," 2002 IEEE MTT-S Int. Mic. Sym. Digest, vol. 2, pp. 1075-1078, Jun. 7, 2002.

Hans et al. disclosed a plastic PBG guide with a solid polyethylene core and surrounding an equal-sized honeycomb sheath for terahertz pulse propagation. However, the measured loss is high, greater than 5 decibels per centimeter (dB/cm) at 400 gigahertz (GHz).

The above-mentioned PBG guides are typically used for fiber optic communications. However, such PBG guides are not suitable for use in terahertz endoscopes and fiberscopes. Accordingly, a need exists for an apparatus and method that provides a low-loss radio-frequency (RF) waveguide structures between sub-millimeter (300 GHz) and far-infrared (30 THz).

SUMMARY OF THE INVENTION

The present invention provides a system and a method that overcomes the aforementioned limitations and fills the aforementioned needs by providing a method and apparatus for ultra-low loss RF waveguide structures targeted between 300 GHz and 30 THz.

This new structure uses a hollow core rather than the solid core of Han et al., thereby reducing losses and making long path length propagation possible for both endoscope or fiberscope operation. It also allows low-loss single mode propagation of energy in the frequency range from 300 GHz to 30 THz, as well as simple coupling into and out of fundamental mode waveguide horns that are inserted in the core of the guide in order to launch into the fiber.

The low-loss RF waveguide comprises a hollow core and a flexible honeycomb, periodic-bandgap structure surrounding the hollow core. The low-loss RF waveguide is formed to operate between 300 GHz and 30 THz.

Additionally, the flexible honeycomb, periodic-bandgap structure comprises a plurality of tubes having approximately equal size. The tubes are composed of a material selected from a group consisting of low-loss quartz, polyethylene, and high-resistivity silicon. In another aspect, the hollow core is over-moded and has a circular cross-section.

In another aspect, a ribbon-guide is positioned within the hollow core such that the hollow core has a first cross-sectional dimension and a second cross-sectional dimension, wherein the first cross-sectional dimension is not equal to the second cross-sectional dimension.

In yet another aspect, the present invention further comprises a conical feedhorn attached with the hollow core.

The present invention also relates to a fiberscope. The fiberscope comprises a low-loss RF waveguide and a terahertz signal source coupled with the low-loss RF waveguide. The low-loss RF waveguide includes a hollow core and a flexible honeycomb, periodic-bandgap structure surrounding the hollow core. Additionally, the low-loss RF waveguide is configured to operate between 300 GHz and 30 THz. A beam splitter is located within the low-loss RF waveguide for polarizing a signal passed through the waveguide. A terahertz signal receiver is coupled with the beam splitter to receive a reflected signal.

In another aspect, a conical feedhorn is attached with the hollow core and positioned between the low loss-RF waveguide and the terahertz signal source.

In another aspect, the present invention includes a method for guiding RF signals. The method comprises acts of forming a flexible honeycomb, periodic-bandgap structure around a hollow core, resulting in a low-loss RF waveguide, such that the RF waveguide is operable for receiving RF signals in the range of approximately 300 GHz to approximately 30 THz.

The act of forming includes an act of arranging tubes of approximately equal size to form the flexible honeycomb, periodic-bandgap structure. Additionally, the act of arranging includes an act of selecting and forming the tubes of a material selected from a group consisting of low-loss quartz, polyethylene, and high-resistivity silicon. The act of forming further includes an act of arranging the flexible honeycomb, periodicic-bandgap structure such that the hollow core has a circular cross-section.

In another aspect, the act of forming further includes an act positioning a ribbon-guide within the hollow core such that the hollow core has a first cross-sectional dimension and a second cross-sectional dimension, whereby the first cross-sectional dimension does not equal the second cross-sectional dimension.

In another aspect, the method further comprises acts act of coupling a terahertz signal source to the low-loss RF waveguide; and coupling a conical feedhorn between the terahertz signal source and the low-loss RF waveguide such that the conical feedhorn fits into the hollow core.

In yet another aspect, the method further comprises acts of inserting a beam splitter into the low-loss RF waveguide; and coupling a terahertz signal receiver to the beam splitter.

The present invention also relates to a method of imaging, comprising acts of utilizing the low-loss RF waveguide; passing a signal having a frequency in the range of 300 GHz to 30 THz into the low-loss RF waveguide; reflecting the signal off of an object, resulting in a reflected signal; and receiving the reflected signal. The act of receiving the reflected signal further comprises acts of utilizing a beam splitter inserted into the low-loss RF waveguide; and receiving the reflected signal with a receiver coupled with the beam splitter.

Finally, in the act of utilizing a low-loss RF waveguide, the RF waveguide includes a ribbon-guide positioned within the hollow core.

BRIEF DESCRIPTION OF THE DRAWNGS

The objects, features and advantages of the present invention will be apparent from the following detailed descriptions of the various aspects of the invention in conjunction with reference to the following drawings, where:

DETAILED DESCRIPTION

Figure 1:
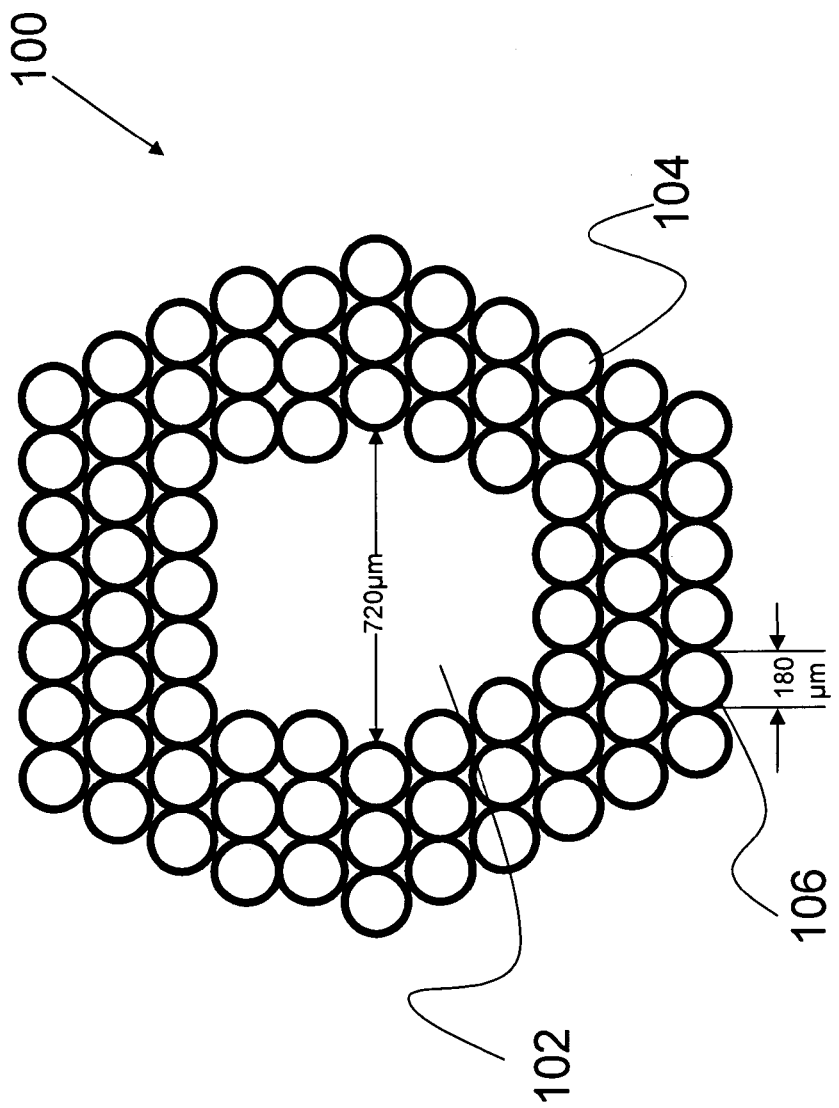
FIG. 1 is a cross-sectional illustration a low-loss RF waveguide according to the present invention.

The present invention relates to the field of radio-frequency (RF) waveguides. More specifically, the present invention pertains to a method and apparatus that provides ultra-low-loss RF waveguide structures targeted between 300 GHz and 30 THz. The following description, taken in conjunction with the referenced drawings, is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein. Furthermore, it should be noted that, unless explicitly stated otherwise, the figures included herein are illustrated diagrammatically and without any specific scale, as they are provided as qualitative illustrations of the concept of the present invention.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" in the claims herein is not intended to invoke the provisions of 35 U.S.C. Section 112, Paragraph 6.

Below, a brief introduction is provided in the form of a narrative description of the present invention to give a conceptual understanding prior to developing the specific details. Next, a detailed explanation of various aspects is provided in order to enable the reader to make and use the various embodiments of the invention without involving undue experimentation.

(1) Introduction

Disclosed herein is a new class of ultra-low-loss radio frequency (RF) waveguide structures targeted at frequencies between approximately 300 gigahertz (GHz) and 30 terahertz (THz), also referred to as the "Terahertz Gap." The guide medium takes the form of a hollow-core, periodic-bandgap (HC-PBG) structure. The HC-PBG structure includes a honeycomb array of tubes around an oversized (multi-mode) hollow core.

The geometric arrangement of the HC-PBG structure and the selected materials provide for a HC-PBG structure being operable over a much wider wavelength range than other HC-PBG structures. The surrounding honeycomb periodic-bandgap structure possesses band-gap/stop behavior for fields of the guided wave penetrating into that structure, resulting in the confinement of the wave within the central core or hole over a desired propagation band. The hollow core and the honeycomb periodic structure results in the propagating fields lying almost entirely in air, thereby providing propagating fields that have minimal absorptive loss. Compared to existing guide media, the HC-PBG structure has lower propagation loss in the terahertz region by several orders of magnitude. Existing guide media are typically formed from metallic or dielectric waveguide. For such existing waveguides, resistive skin effect loss in non-perfect conductors and vibrational phonon absorptive loss in dielectrics combine to make low-loss RF propagation impossible.

Further, the disclosed HC-PBG structure provides a flexible, low-loss guide medium for terahertz frequencies (i.e., wavelengths from roughly 1 mm to 10 microns). As a non-limiting example, the disclosed HC-PBG structure can be utilized in the development of THz endoscopes and fiberscopes, opening up the first in-vivo use of terahertz signals. Other exemplary uses for the guide medium include low-loss, flexible THz waveguides for efficient sensor and source coupling; chip-to-chip RF interconnects; reconfigurable beam waveguides; and any application where guided RF power distribution is desired. Additionally, the present invention includes a system and method for efficient input/output coupling for RF excitation and detection as well as a mechanism of combining the HC-PBG with an alternate low-loss RF guide concept (i.e., inclusion of a terahertz ribbon).

(2) Detailed Explanation

FIG. 1 depicts a cross-sectional view of one aspect of a low-loss RF waveguide 100. The low-loss RF waveguide 100 comprises a hollow core 102 and a honeycomb, periodic-bandgap structure 104. In this aspect, as a non-limiting example, the diameter of the hollow core 102 is approximately 720 micrometers. As can be appreciated by one skilled in the art, the dimensions described herein are for illustrative purposes only and are not intended to be limiting thereto. The diameter of each of the tubes 106 making up the honeycomb periodic bandgap structure 104 is approximately 180 micrometers ($\mu$m). Although individual tubes 106 can differ in size, it is desirable that the tubes 106 be equally-sized. In the above dimensions, the overall diameter of the low-loss, flexible waveguide 100 is approximately 2 millimeters. A small overall diameter allows for flexible movement when the honeycomb, periodic-bandgap structure 104 is made of a plastic. Alternatively, the small overall diameter provides a slightly more restrictive movement when the honeycomb, periodic-bandgap structure 104 is made from silicon or quartz.

The dimensions provided in FIG. 1 have been optimized for 2.5 THz operation. Optimization for other frequency ranges can be obtained by direct scaling or using a finite-difference time-domain (FDTD) code. Geometric shape, configuration, and aperture dimensions may be adjusted to optimize propagation and stop bands as well as matching into and out of feedhorns. Further, materials selected may be altered in order to optimize the low-loss RF waveguide for other frequency ranges. For example, non-uniform PBG sheath characteristics (such as size and index variations) may be used to optimize mode confinement and purity.

The hollow core 102 is over-moded and has a circular cross-section. The tubes 106 comprising the honeycomb, periodic-bandgap structure 104 may be manufactured from a variety of materials, non-limiting examples of which include low-loss quartz tubing, polyethylene or high-resistivity silicon. The geometry, size, and spacing of the tubes 106 may be varied in order to optimize the low-loss RF waveguide 100 for any of a variety of frequencies from approximately 300 GHz to 30 THz. In one aspect, it is desirable for the tubes 106 to have approximately equal cross-sectional geometry.

In order to launch a single confined mode into the PBG core, a conical feedhorn is inserted fully into the central hole of the PBG structure. Coupling out of the PBG guide is accomplished in the same manner. The feedhorn taper and aperture diameter are designed to match the PBG core 102 diameter. Simulations using FDTD analysis show good matching into the waveguide with this arrangement. A non-limiting example of such a feedhorn includes a simple, dual-mode Pickett-Potter horn. The Picket-Potter horn was described in the following publication: "Characterization of a Dual Mode Horn for Sub-millimeter Wavelengths," IEEE Trans. Microwave Theory and Techniques, vol. MTT-32, no. 8, Aug. 1984, pp. 936-8.

Figure 2:
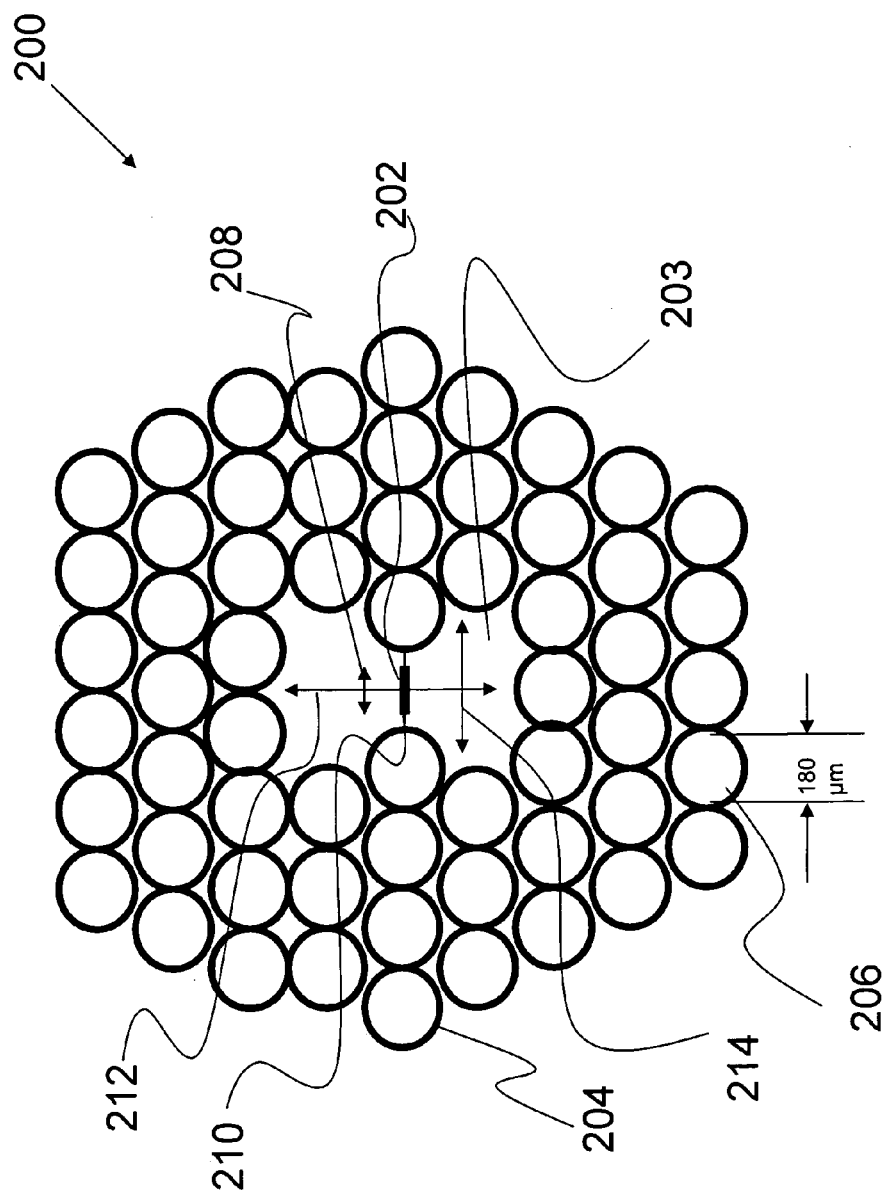
FIG. 2 is a cross-sectional illustration of a hybrid structure according to the present invention.

FIG. 2 depicts a cross-sectional view of another aspect of the present invention. FIG. 2 illustrates a hybrid structure 200 comprising a dielectric ribbon-guide 202 supported by a honeycomb, periodic-bandgap structure 204 (formed of a plurality of tubes 206). Variations to the core structure result in a hybrid structure 200 which combines the properties of a THz ribbon-guide and a hollow-core, periodic-bandgap guide. This ribbon-guide 202 can be composed of any suitable dielectric material, non-limiting examples of which include high resistivity silicon, quartz, low-loss plastic such as polyethylene or polypropylene, kapton, polyethylene and polypropylene. For example, a quartz ribbon can be utilized that is formed gluing together 10 circular fibers of 100 micron diameter to form a 1000×100 micron cross section ribbon.

The ribbon-guide 202 is positioned within the hollow core 203 such that the hollow core has a first cross-sectional dimension 212 that is not equal to a second cross-sectional dimension 214. The ribbon-guide 202 has a dimension in a first direction 208 (width) of approximately one-half wavelength, and a dimension in a second direction 210 (thickness) of approximately a tenth of a wavelength. In this aspect, the propagating mode is pinned to the ribbon-guide 202, reducing the hollow core 203 diameter 212 to 2-5 wavelengths. The honeycomb, periodic-bandgap structure 204 provides the isolation required to handle the waveguide while retaining the flexibility and low-loss guiding properties. Some advantages of this embodiment are greater design freedom and a smaller cross-sectional area.

The low-loss RF waveguide of the present invention can be used in a variety of applications, such as in-vivo imaging with endoscope and fiberscope tools, long length terahertz propagation in an undisturbed environment, and vacuum propagation (by sealing off and pumping out the core). The geometry, size, and spacing of the tubes 106 (as shown FIG. 1) and 206 (as shown in FIG. 2) may be optimized to provide continuous wave propagation of narrow frequency bands. For example, the low-loss RF waveguides may be optimized for use in narrow frequency bands centered around 2.5 THz and 650 GHz, two frequencies that are known to be useful for imaging applications in the submillimeter area. An advantage of the low-loss RF waveguides is that they can bend or twist without distorting internal fields, which is not possible with metallic waveguides or fixed optical beams.

Figure 3:
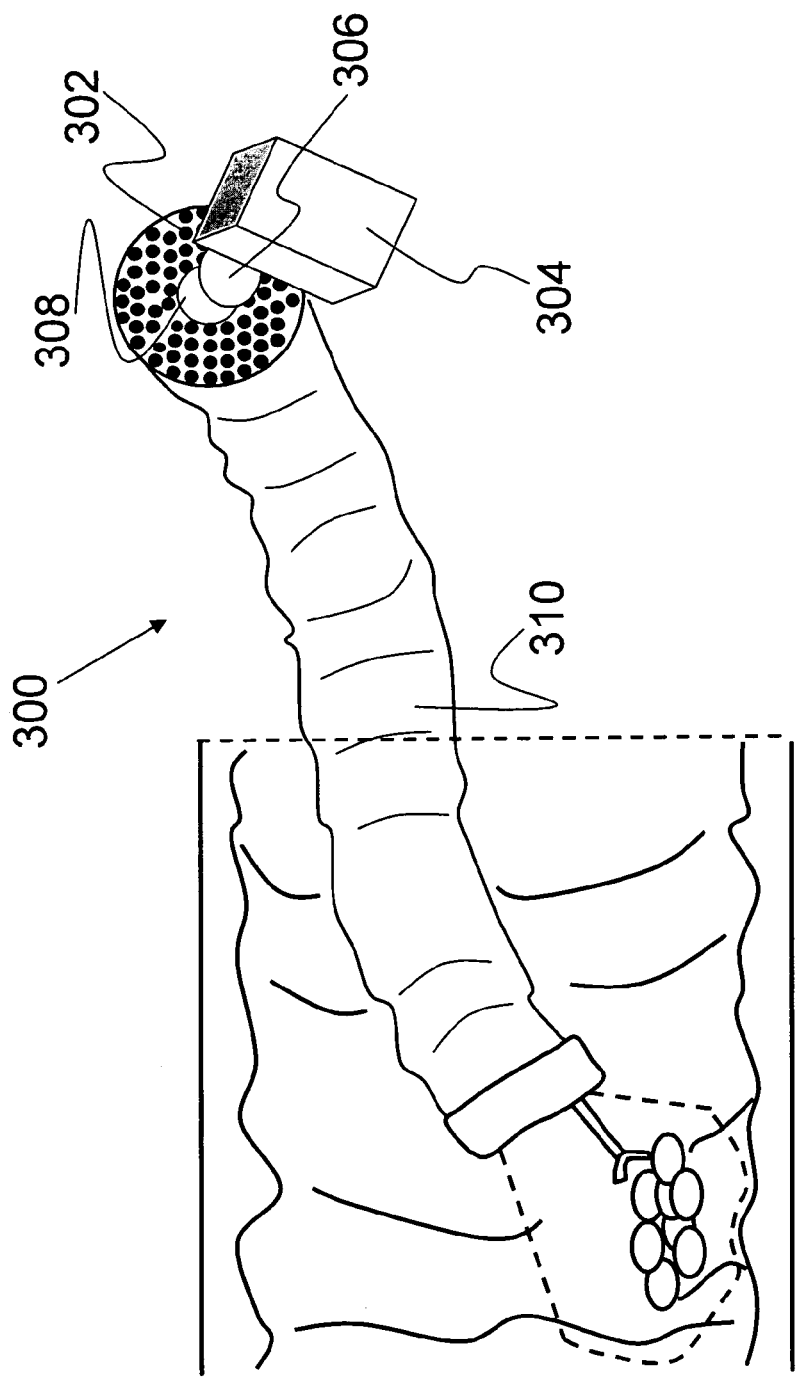
FIG. 3 is an illustration of an exemplary application of the present invention.

An example of one application is shown in FIG. 3, which depicts a first THz fiberscope 300. The THz fiberscope comprises a low-loss RF waveguide 302 coupled with a THz signal source (multiplier) 304 that injects an RF signal directly into the hollow core 308. In this aspect, the THz signal source 304 has a waveguide horn 306 which fits inside the hollow core 308 of the low-loss RF waveguide 302. A return signal is picked up by a second THz fiberscope where the THz signal source 304 is replaced with a THz signal receiver. In this aspect, a parallel HC-PBG waveguide (second fiberscope) port is inserted into the fiberscope 300 (or endoscope) with an external detector on the output side (also coupled into the HC-PBG guide using an inserted feed horn).

The feedhorn is a mode launching antenna. The feedhorn takes input power from a source (which can be a waveguide, transmission line or active power generator) and gradually converts the power into a propagating mode that matches to a plane wave in free space. Typically, the designation "feed" refers to the fact that the horn is matching or feeding the power to some other beam forming network (like a parabolic antenna in the case of a radio telescope), or to free space. The "horn" portion indicates that the geometric form is similar to that of a sound forming wind instrument. Essentially, it provides the same function, matching the sound wave in the instrument to free space for maximum transmitted power. Horns are typically either conical or pyramidal, but they can take many other shapes as well, depending on the input/output fields being propagated/generated. Although other horn shapes can be used in the present invention, a conical horn (the most common millimeter wave power launcher) is desirable because it matches the PBG guide core and launches a nice propagating Gaussian mode in to the PBG guide itself.

Figure 4:
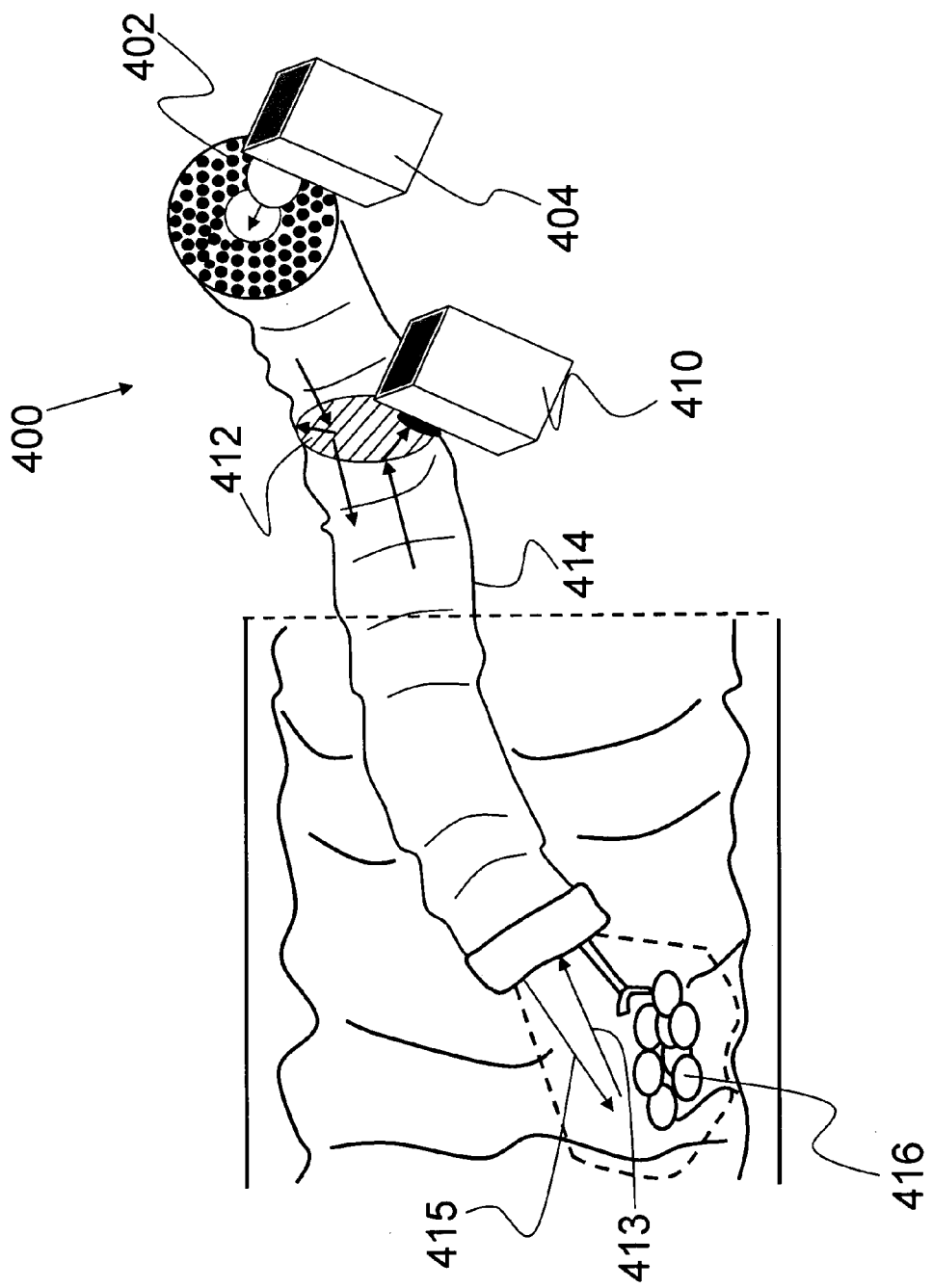
FIG. 4 is an illustration of an exemplary application of the present invention.

FIG. 4 depicts another exemplary THz fiberscope 400. As shown in FIG. 4, the THz fiberscope 400 comprises a low-loss RF waveguide 402 coupled with a THz signal source 404 and a THz signal receiver 410. Additionally, the low-loss RF waveguide 402 comprises a beam splitter 412, such as a polarizing beam splitter. As a non-limiting example, the beam splitter 412 is a 45 degree wire-grid beam splitter. Using the beam splitter 412, the THz signal source 404 may transmit one polarization signal (having a frequency) 415 to be reflected by an object 416, while the reflection of the THz signal 413 will be in another polarization signal. In this aspect, the beam splitter 412 can separate the polarization and ensure that the reflected signal 413 is passed to the THz signal receiver 410.

For applications in in-vivo imaging via a fiberscope or an endoscope, the low-loss RF waveguide 302 may be sealed in a commercially or specially fabricated insertion tube 310 (FIG. 3) or 414 (FIG. 4), with a thin resonant window (not shown). The resonant window is located at the end where the THz source 304 and 404 connects with the low-loss RF waveguide 302 or 402. Using the fiberscope or endoscope, imaging can be performed with fixed frequencies or with chirped or scanned frequencies providing depth and/or spectroscopic information.

Figure 5:
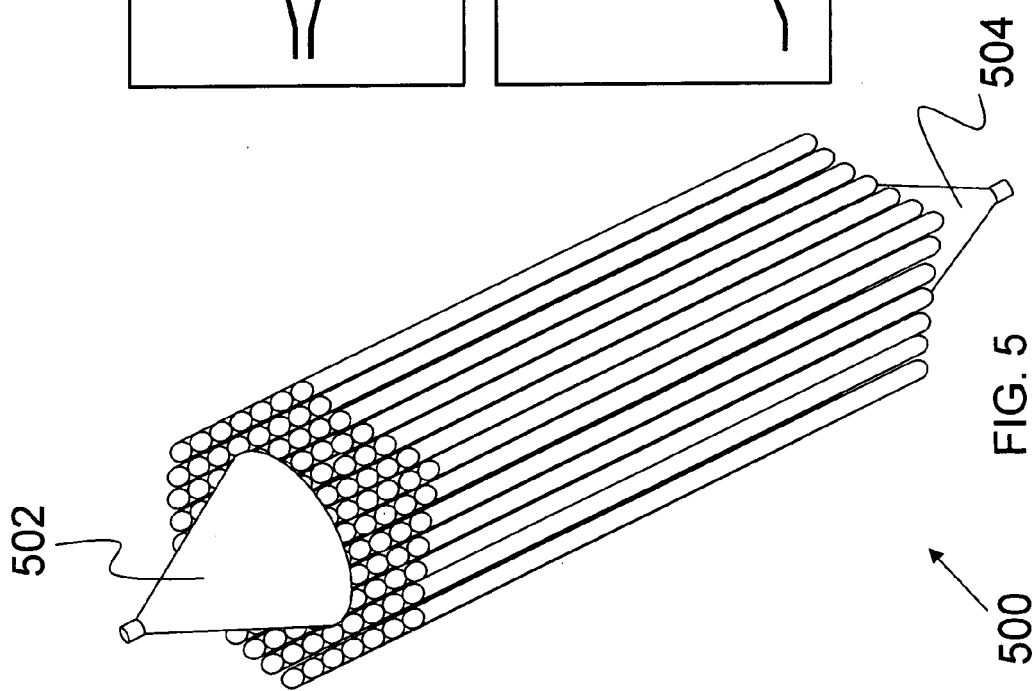
FIG. 5 is an illustration of a hollow-core, periodic-bandgap (HC-PBG) structure according to the present invention, with input and output horns to launch a desired mode.

FIG. 5 shows an exemplary arrangement of a PBG guide 500 with an input horn 502 and an output horn 504 to launch the desired HE11 mode. A mode is the particular geometric field pattern that propagates the pattern through the device. HE11 is the electrostatic field (E-field) vertical/magnetic field (H-field) horizontal, Gaussian power distribution (center-to-edge) that propagates from a typical conical or pyramidal quality feed horn. As shown in FIG. 5, the horns 502 and 504 are conical in shape and cover the hollow core. Although also conical, due to the orientation of the illustration in FIG. 5, the conical portion of the output horn 504 is not shown.

Figure 6A:
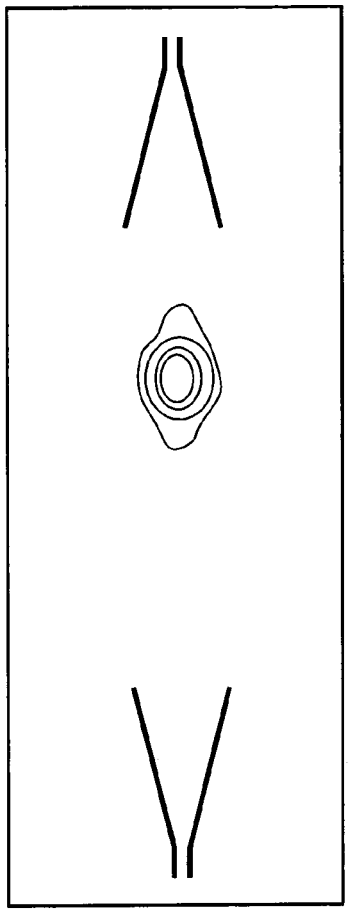
FIG. 6A is an illustration of an exemplary analysis indicating a low dispersion propagating mode with a confined electrostatic field (E plane field)
Figure 6B:
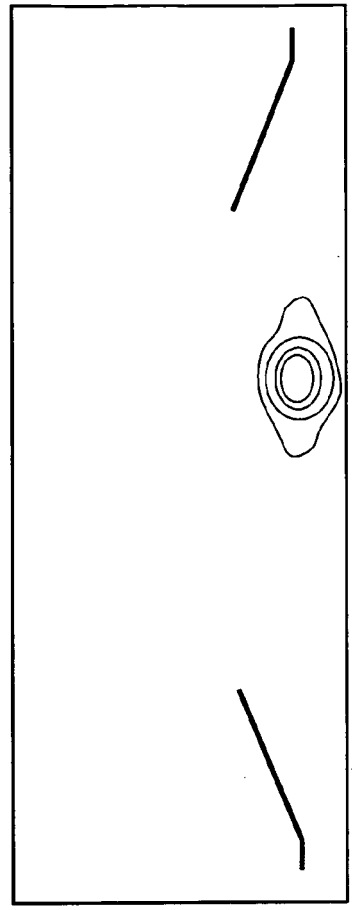
FIG. 6B is an illustration of an exemplary analysis indicating a low dispersion propagating mode with a confined magnetic field (H plane field)

FIGS. 6A and 6B depict an analysis of field confinement using waveguide horns to launch a desired mode. As shown in FIG. 6A, the analysis indicates a low dispersion propagating mode with a confined electrostatic field (E plane field). Additionally, FIG. 6B depicts an analysis indicating a low dispersion propagating mode with a confined magnetic field (H plane field).

Figure 7B:
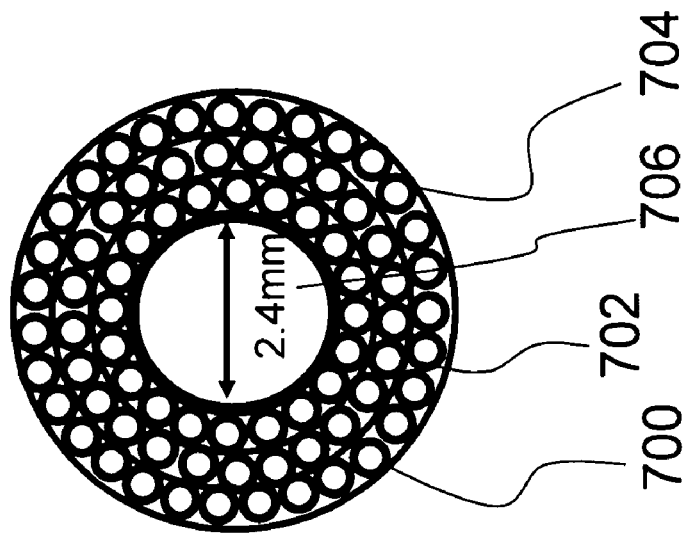
FIG. 7B is an illustration of an exemplary HC-PBG structure for operation at 1200 GHz.
Figure 7A:
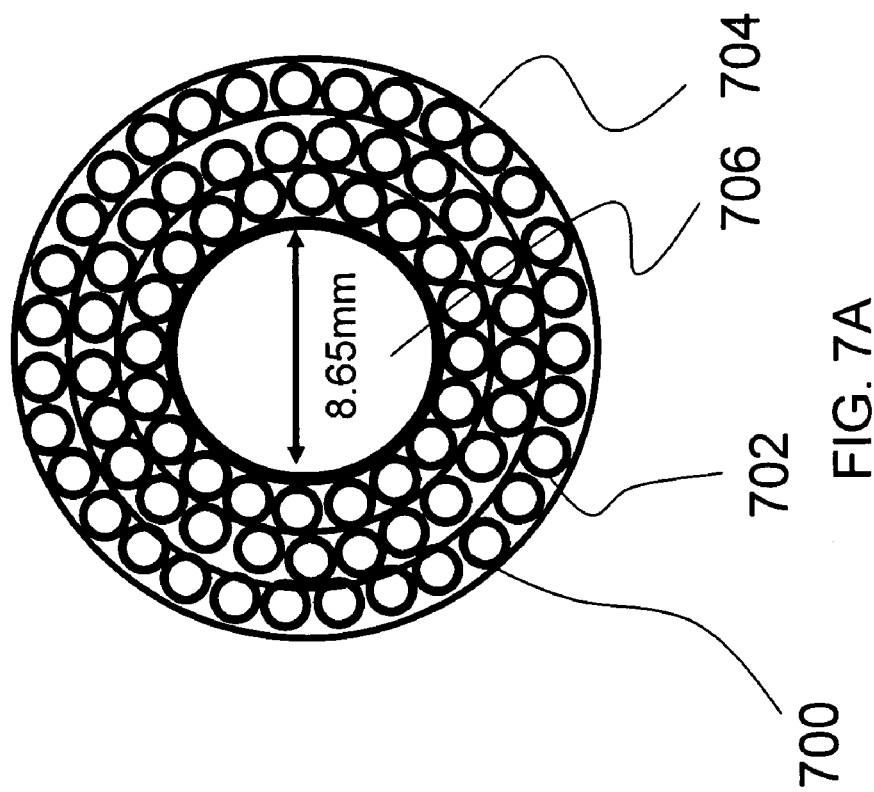
FIG. 7A is an illustration of an exemplary HC-PBG structure for operation at 350 GHz.

FIGS. 7A and 7B depict exemplary HC-PBG guides 700 for operation at 350 GHz and 1200 GHz respectively. In these examples, the HC-PBG guide 700 was fabricated from commercially available Teflon tubes 702 wrapped with thin Teflon tape 704 around a hollow Teflon tube core 706. As shown in FIG. 7B, the smaller tubes 702 and smaller diameter of the tube core 706 provide for higher GHz operation.

What is claimed is:

1. A low-loss RF waveguide, comprising:
    a hollow core;
    a flexible honeycomb, periodic-bandgap fiber surrounding the hollow core, wherein the low-loss RF waveguide is formed to operate in a range of approximately 300 GHz to approximately 30 THz; and
    a dielectric ribbon-guide positioned within the hollow core such that the hollow core has a first cross-sectional dimension and a second cross-sectional dimension, wherein the first cross-sectional dimension is not equal to the second cross-sectional dimension.

2. A low-loss RF waveguide as set forth in claim 1, wherein the flexible honeycomb, periodic-bandgap fiber comprises a plurality of tubes having approximately equal cross-sectional geometry.

3. A low-loss RF waveguide as set forth in claim 2, wherein the tubes are formed of a material selected from a group consisting of low-loss quartz, polyethylene, and high-resistivity silicon.

4. A low-loss RF waveguide as set forth in claim 1, wherein the hollow core is over-moded.

5. A low-loss RF waveguide as set forth in claim 1, wherein the flexible honeycomb, periodic-bandgap fiber is composed of material a selected from a group consisting of low-loss quartz, polyethylene, and high-resistivity silicon.

6. A low-loss RF waveguide as set forth in claim 1, wherein the hollow core has a substantially circular cross-section.

7. A low-loss RF waveguide as set forth in claim 1, further comprising a conical feedhorn attached with the hollow core.

8. A low-loss RF waveguide, comprising:
a hollow core;
a flexible honeycomb, periodic-bandgap fiber surrounding the hollow core;
a dielectric ribbon-guide positioned within the hollow core such that the hollow core has a first cross-sectional dimension and a second cross-sectional dimension, wherein the first cross-sectional dimension is not equal to the second cross-sectional dimension; and
wherein the low-loss RF waveguide is formed to operate in a range of approximately 300 GHz to approximately 30 THz;
wherein the flexible honeycomb, periodic-bandgap fiber comprises a plurality of tubes having approximately equal cross-sectional geometry;
wherein the tubes are formed of a material selected from a group consisting of low-loss quartz, polyethylene, and high-resistivity silicon;
wherein the hollow core is over-moded; and
wherein the hollow core has a substantially circular cross-section.

9. A fiberscope comprising:
a low-loss RF waveguide, comprising:
a hollow core;
a flexible honeycomb, periodic-bandgap fiber surrounding the hollow core, wherein the low-loss RF waveguide operates in a range of approximately 300 GHz to approximately 30 THz;
a dielectric ribbon-guide positioned within the hollow core such that the hollow core has a first cross-sectional dimension and a second cross-sectional dimension, wherein the first cross-sectional dimension is not equal to the second cross-sectional dimension; and
a terahertz signal source coupled with the low-loss RF waveguide.

10. A fiberscope as set forth in claim 9, further comprising a conical feedhorn attached with the hollow core and positioned between the low loss-RF waveguide and the terahertz signal source.

11. A fiberscope as set forth in claim 10, further comprising:
a beam splitter located within the low-loss RF waveguide; and
a terahertz signal receiver coupled with the beam splitter.

12. A method for guiding RF signals, the method comprising acts of:
forming a flexible honeycomb, periodic-bandgap fiber around a hollow core; and
positioning a dielectric ribbon-guide within the hollow core such that the hollow core has a first cross-sectional dimension and a second cross-sectional dimension, wherein the first cross-sectional dimension is not equal to the second cross-sectional dimension; resulting in a low-loss RF waveguide such that the RF waveguide is operable for receiving RF signals in the range of approximately 300 GHz to approximately 30 THz.

13. A method as set forth in claim 12, wherein the act of forming includes an act of arranging tubes of approximately equal size to form the flexible honeycomb, periodic-bandgap fiber.

14. A method as set forth in claim 13, wherein the act of arranging includes an act of selecting the tubes formed of a material selected from a group consisting of low-loss quartz, polyethylene, and high-resistivity silicon.

15. A method as set forth in claim 12, wherein the act of forming includes an act of manufacturing the flexible honeycomb, periodic-bandgap fiber from a material selected from a group consisting of low-loss quartz, polyethylene, and high-resistivity silicon.

16. A method as set forth in claim 12, wherein the act of forming further includes an act of arranging the flexible honeycomb, periodic-bandgap fiber such that the hollow core has a circular cross-section.

17. A method as set forth in claim 12, further comprising an act of coupling a terahertz signal source to the low-loss RF waveguide.

18. A method as set forth in claim 17, further comprising an act of coupling a conical feedhorn between the terahertz signal source and the low-loss RF waveguide such that the conical feedhorn fits into the hollow core.

19. A method as set forth in claim 12, further comprising acts of:
inserting a beam splitter into the low-loss RF waveguide; and
coupling a terahertz signal receiver to the beam splitter.

20. A method of imaging, the method comprising acts of:
utilizing a low-loss RF waveguide, where the low-loss RF waveguide comprises:
a hollow core;
a flexible honeycomb, periodic-bandgap fiber surrounding the hollow core; and
a dielectric ribbon-guide positioned within the hollow core such that the hollow core has a first cross-sectional dimension and a second cross-sectional dimension, wherein the first cross-sectional dimension is not equal to the second cross-sectional dimension;
passing a signal having a frequency in the range of approximately 300 GHz to approximately 30 THz into the low-loss RF waveguide;
reflecting the signal off of an object, resulting in a reflected signal; and receiving the reflected signal.

21. A method as set forth in claim 20, wherein the act of receiving the reflected signal further comprises acts of:
utilizing a beam splitter inserted into the low-loss RF waveguide; and
receiving the reflected signal with a receiver coupled with the beam-splitter.

* * * * *